| 
US007241388B2

(12) United States Patent
Koslow

(10) Patent No.: US 7,241,388 B2
(45) Date of Patent: *Jul. 10, 2007

(54) MEANS TO MINIATURIZE DIFFUSION FILTERS FOR PARTICULATE REMOVAL

(75) Inventor: Evan E. Koslow, Weston, CT (US)

(73) Assignee: KX Industries L.P., Orange, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/308,695

(22) Filed: Dec. 3, 2002

(65) Prior Publication Data

US 2004/0084378 A1    May 6, 2004

Related U.S. Application Data

(63) Continuation-in-part of application No. 10/286,695, filed on Nov. 1, 2002, and a continuation-in-part of application No. 10/290,803, filed on Nov. 8, 2002, now Pat. No. 6,630,016.

(51) Int. Cl.
*B01D 61/00* (2006.01)
*B01D 29/00* (2006.01)
*B01D 39/00* (2006.01)
*B01D 15/00* (2006.01)
*C02F 9/00* (2006.01)

(52) U.S. Cl. .............. 210/650; 210/502.1; 210/257.2; 210/262; 210/767

(58) Field of Classification Search ................ 210/767, 210/644, 502.1, 506, 262, 277, 278, 663, 210/652, 257.2, 232; 62/125
See application file for complete search history.

(56) References Cited

U.S. PATENT DOCUMENTS

| 5,221,473 | A | * | 6/1993 | Burrows | 210/232 |
| 5,554,288 | A | * | 9/1996 | Rydell et al. | 210/504 |
| 6,182,453 | B1 | * | 2/2001 | Forsberg | 62/125 |
| 6,190,558 | B1 | * | 2/2001 | Robbins | 210/652 |
| 6,630,016 | B2 | * | 10/2003 | Koslow | 95/285 |

* cited by examiner

*Primary Examiner*—Ana M. Fortuna
(74) *Attorney, Agent, or Firm*—DeLio & Peterson, LLC; Robert Curcio; Gary Warner

(57) ABSTRACT

The present invention is directed to a filtration system including filter media that use diffusion as a method of particulate reduction that balances the contact time required for a desirable level of interception and filter performance. The filter system of the present invention includes a filter medium that removes particulate contaminants by diffusion, means for providing sufficient contact time for an influent to contact the filter medium such that the filter medium can intercept sub-micron particulates at an average flow rate below that of an on-demand or instantaneous flow rate; and a storage buffer for providing a filtered effluent at a rate independent of the average flow rate required to achieve adequate particulate reduction through the filter medium.

11 Claims, 2 Drawing Sheets

Figure 1:
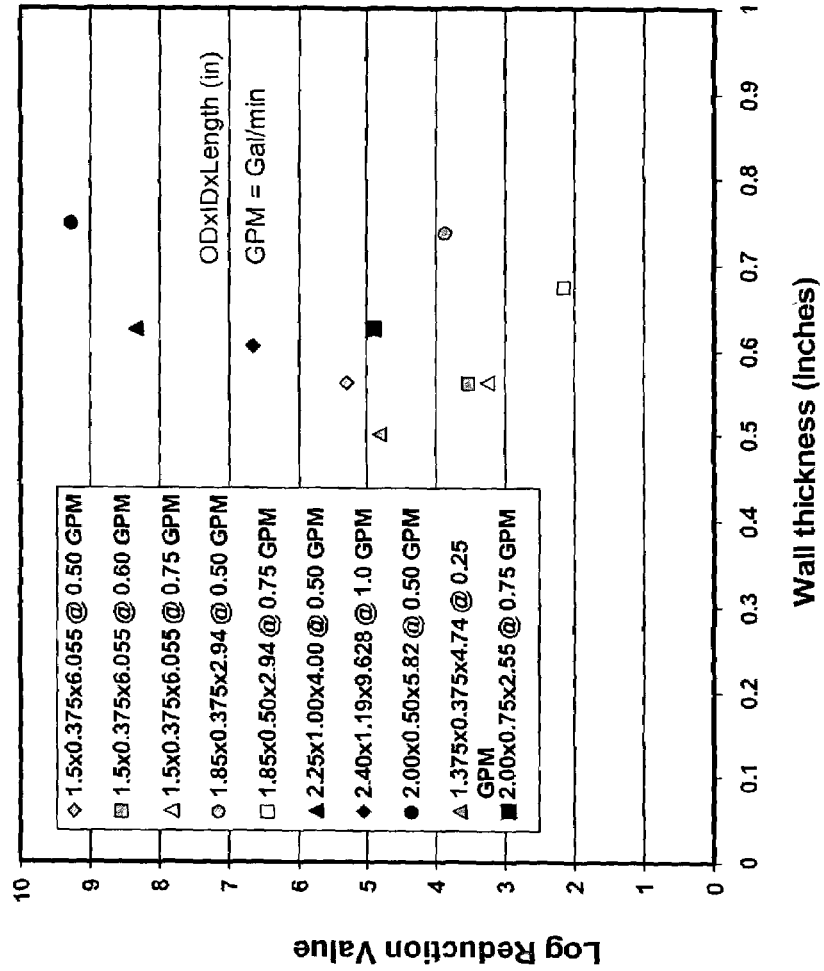

MEANS TO MINIATURIZE DIFFUSION FILTERS FOR PARTICULATE REMOVAL

This application is a continuation-in-part of U.S. application Ser. No. 10/286,695 filed on 1 Nov. 2002, and Ser. No. 10/290,803 filed on 8 Nov. 2002, now U.S. Pat. No. 6,630,016, both of which are incorporated herein by reference.

The present invention is directed to filtration systems that work using diffusive methods and to the removal of particulate contaminants using such filtration systems, including microbiological contaminants.

Particulate contaminants are collected by water filters via the following mechanisms: direct interception and diffusion. Collection of the particulate contaminants take place on the solid elements of the filter. Direct interception occurs when a particle collides head-on with a solid surface imposed on a flow path through the filter. Diffusion occurs when extremely small particles, particularly sub-micron particles, travel in an erratic path due to Brownian motion, thereby augmenting their chances of intersecting the solid elements or surfaces of the filter medium and being adsorbed on these surfaces.

Prior art filters that provide reduction of microbiological contaminants such as *Cryptosporidium* and *Giardia*, have a sufficiently small pore structure to provide direct interception of these contaminants. However, for successful sub-micron or viral interception, the principal mechanism at work is often diffusion because the particles are much smaller than the pores of the filter medium. There must be sufficient contact time for the contaminant to work its way to a solid surface of the filter medium for successful interception via diffusion. Once such a small particle contacts the surface of the pore, it can be retained by coulombic or van der Waals forces or adhesion that are stronger than the local hydrodynamic shear at the surface. While filters that operate by direct interception become progressively more efficient as the thickness of a uniform filter medium becomes progressively greater, this is not true for a filter that operates by diffusion. In this case, contact time plays a pivotal role.

SUMMARY OF THE INVENTION

In a first aspect, the present invention is directed to a filtration system comprising: a filter medium that removes particulate contaminants from a fluid by diffusion; means for providing sufficient contact time for an influent to contact the filter medium such that the filtration system operates at an average flow rate sufficient to achieve a particulate reduction target performance and below a flow rate required by a downstream requirement for a purified fluid; and a storage buffer, downstream from the filter medium, that allows the purified fluid to be supplied at the flow rate required by the downstream requirement for a purified fluid.

In another aspect, the present invention is directed to a filtration system comprising: a filter medium including an interception enhancing agent comprising a cationic material having a counter ion associated therewith, wherein a biologically active metal is precipitated with the counter ion in direct proximity to the cationic material; a flow regulator for providing sufficient contact time of an influent with the filter medium; and a storage buffer for storing a purified effluent to provide on-demand access to the purified effluent independent of the flow rate through the filter medium needed to achieve a required contact time.

In yet another aspect, the present invention is directed to a method of providing a purified fluid on-demand comprising the steps of: providing a filtration system including a filter medium that removes particulate contaminants by diffusion; operating the filtration system at an average flow rate below that of a rate demanded by a user such that a sufficient contact time is provided for adequate diffusive filtration; and collecting a purified fluid in a storage vessel to buffer an intermittent instantaneous demand independent from the average flow rate through the filter medium.

BRIEF DESCRIPTION OF DRAWINGS

FIG. 1 shows that the MS2 viral particle reduction has no clear relationship with the thickness of the filter wall.

FIG. 2 shows that the MS2 viral particles interception closely responds instead to the contact time of the fluid in contact with the filter medium.

DETAILED DESCRIPTION OF THE PREFERRED EMBODIMENT(S)

The present invention is directed to a filter system that removes submicron particulate contaminants, including bacteria and viruses, by diffusion. Rather than increasing the thickness or size of the filter medium, the present invention includes a means for providing sufficient contact time for successful interception of sub-micron particulates without compromising on-demand performance or integrity of the system.

The filter system of the present invention includes a filter medium that removes small particulate contaminants by diffusion, means for providing sufficient contact time for an influent to contact the filter medium such that the filter system can operate at an average flow rate below that of peak demand through a storage buffer. The average flow rate through the filter medium is thereby maintained at a sufficient contact time to provide the desired level of interception without sacrificing the ability to meet brief flow rate demands much greater than this average flow rate.

The Filter Medium

A filter medium useful in the present invention operates by diffusion, wherein the small contaminants travel in an erratic path that increases the chances of the contaminants coming in contact with a solid surface of the filter medium even though the pore size of the filter medium is larger than the size of the contaminants. The slower the fluid flow, the more time the particles have to diffuse to the surface of the pores within the filter medium, thereby giving it a much better chance of hitting and sticking to a surface of the filter medium. When particles are removed from a fluid stream by direct interception, the flow rate and contact time within the filter medium has almost no impact on the removal of particles by the filter. In these cases, only the thickness of the filter medium will significantly impact the performance of the filter.

Preferably, the filter medium is microporous with a pore structure that provides short diffusion distances from the fluid to the surface of the filter medium. For successful microbiological interception, the filter medium preferably has a mean flow path of less than about 4 microns, more preferably, less than about 2 microns, and can be less than about 1 micron. To further enhance interception of microbiological contaminants, at least a portion of the filter medium is charge modified and treated with a biologically active agent. Charge modification of the filter medium can comprise a chemical treatment process used to treat the surfaces of the microporous structure with a cationic material. The charge provided by the cationic material aids in electro-kinetic interception of microbiological contaminants, while the tight pore structure provides a short diffusion path and, therefore, rapid diffusion kinetics of particulates in a flowing fluid to the surface of the microporous structure. The addition of a biologically active metal to a cationic material having a counter ion associated therewith can also provide broad-spectrum reduction of microbiological contaminants on contact. Biologically active agents useful in treating the filter medium are known to one of skill in the art.

The filter medium can be made from a number of different materials such as, for example, membranes, nanofibers, and small particles and powders immobilized in a solid structure. Such filter media can be comprised of organic or inorganic materials including, but not limited to, polymers, ion-exchange resins, engineered resins, ceramics, cellulose, rayon, glass, metal, activated alumina, activated carbon, silica, zeolites, diatomaceous earth, activated bauxite, fuller's earth, calcium hydroxyappatite, titanates and other materials, or combinations thereof. Combinations of organic and inorganic materials are contemplated and within the scope of the invention. Such filter media may be made using methods known to one of skill in the art.

The filter medium can also be comprised of a plurality of nanofibers including whiskers or micro-particulate ingredients, of organic and inorganic materials including, but not limited to, polymers, ion-exchange resins, engineered resins, ceramics, cellulose, rayon, glass, metal, activated alumina, carbon or activated carbon, silica, zeolites, diatomaceous earth, activated bauxite, fuller's earth, calcium hydroxyappatite, other adsorbent materials, or combinations thereof. Combinations of organic and inorganic fibers and/or whiskers or micro-particles are contemplated and within the scope of the invention as for example, glass, ceramic, or metal fibers and polymeric fibers may be used together with very small particles incorporated into the filter medium.

When produced by a wet laid process from nanofibers such as cellulose or polymer fibers, such fibers should also have a Canadian Standard Freeness of less than or equal to about 100, and most preferably equal to about 45, or less. Preferably, a significant portion of the fibers should have a diameter less than or equal to about 1000 nanometers, more preferably less than or equal to about 400 nanometers, and fibers less than or equal to about 250 nanometers in diameter are most preferred. It is preferable to chop the fibers to a length of about 1 millimeter to about 8 millimeters, preferably about 2 millimeters to about 6 millimeters, and more preferably about 3 millimeters to about 4 millimeters. Fibrillated fibers are most preferred due to their exceptionally fine dimensions and potentially low cost.

Preferably, fibrillated synthetic cellulose fibers can produce an ultrafine, hydrophilic filter medium. Such fibrillated cellulose fibers can be made by direct dissolution and spinning of wood pulp in an organic solvent, such as an amine oxide, and are known as lyocell fibers. Lyocell fibers have the advantage of being produced in a consistent, uniform manner, thus yielding reproducible results, which may not be the case for, for example, natural cellulose fibers. Further, the fibrils of lyocell are often curled. The curls provide a significant amount of fiber entanglement, resulting in a finished filter medium with high dry strength and significant residual wet strength. Furthermore, the fibrillated lyocell fibers may be produced in large quantities using equipment of modest capital cost. It will be understood that fibers other than cellulose may be fibrillated to produce extremely fine fibrils, such as for example, artificial fibers, in particular, acrylic or nylon fibers, or other natural cellulosic materials. Combinations of fibrillated and non-fibrillated fibers may be used in the filter medium.

The filter medium can also comprise of an array of particles which may also have adsorbent and/or absorbent properties. The array can be a solid composite block, a monolith, a ceramic candle, a flat-sheet composite of bonded or immobilized particles formed into a coherent medium using a binder or supporting fibers, and the like. These particle arrays can be made through processes known in the art such as, for example, extrusion, molding, or slip casting. The active particles can include, but are not limited to, activated carbon, activated alumina, zeolites, diatomaceous earth, silicates, aluminosilicates, titanates, bone char, calcium hydroxyapatite, manganese oxides, iron oxides, magnesia, perlite, talc, polymeric particulates, clay, iodated resins, ion exchange resins, ceramics, super absorbent polymers (SAPs), and combinations thereof.

Enhancing Interception of Microbiological Contaminants

The filter medium can be charge modified and treated with a biologically active agent, that both act as an interception enhancing agent to provide enhanced interception of microbiological particles and other sub-micron contaminants. Treatment of the filter medium with a charge modifier typically creates a strong positive charge upon the treated surfaces as measured using streaming or zeta potential analysis and this positive charge should be retained at pH values below 10. The charge modifier can be a cationic material that is a small charged molecule or a linear or branched polymer having positively charged atoms along the length of the polymer chain having a counter ion associated therewith. The cationic material is adsorbed on at least a portion of the filter medium and a biologically active metal can be precipitated with the counter ion in direct proximity to the cationic material.

If the cationic material is a polymer, the charge density is preferably greater than about 1 charged atom per about every 30 Angstroms, preferably greater than about 1 charged atom per about every 20 Angstroms, and more preferably greater than about 1 charged atom per about every 10 Angstroms of molecular length. The higher the charge density on the cationic material, the higher the concentration of the counter ion associated therewith. A high concentration of an appropriate counter ion can be used to drive the precipitation of the biologically active metal. The high charge density of the cationic material provides the ability to adsorb and significantly reverse the normal negative charge of many raw materials used for the production of filter media.

The use of a cationic polymer of sufficiently high molecular weight allows treatment of the surfaces of the filter medium without serious attendant impact upon any adsorptive capabilities of the mezo-pores and micro-pores of filter medium materials such as activated carbon. The cationic material can have a molecular weight greater than or equal to about 5000 Daltons, preferably greater than or equal to 100,000 Dalton, more preferably greater than or equal to about 400,000 Daltons, and can be greater than or equal to about 5,000,000 Daltons.

The cationic material includes, but is not limited to, quaternized amines, quaternized amides, quaternary ammonium salts, quaternized imides, benzalkonium compounds, biguanides, cationic aminosilicon compounds, cationic cellulose derivatives, cationic starches, quaternized polyglycol amine condensates, quaternized collagen polypeptides, cationic chitin derivatives, cationic guar gum, colloids such as cationic melamineformaldehyde acid colloids, inorganic treated silica colloids, polyamideepichlorohydrin resin, cationic acrylamides, polymers and copolymers thereof, combinations thereof, and the like. Charged molecules useful for this application can be small molecules with a single charged unit and capable of being attached to at least a portion of the filter medium material. The cationic material preferably has one or more counter ions associated therewith which, when exposed to a biologically active metal salt solution, cause preferential precipitation of the metal in proximity to the cationic surface to form a colloidal metal precipitate complex.

Exemplary of amines may be pyrroles, epichlorohydrin derived amines, polymers thereof, and the like. Exemplary of amides may be those polyamides disclosed in International Patent Application No. WO 01/07090, and the like. Exemplary of quaternary ammonium salts may be homopolymers of diallyl dimethyl ammonium halide, epichlorohydrin derived polyquaternary amine polymers, quaternary ammonium salts derived from diamines and dihalides such as those disclosed in U.S. Pat. Nos. 2,261,002, 2,271,378, 2,388,614, and 2,454,547, all of which are incorporated by reference, and in International Patent Application No. WO 97/23594, also incorporated by reference, polyhexamethylenedimethylammonium bromide, and the like. The cationic material may be chemically bonded, adsorbed, or crosslinked to itself and/or to the filter medium material.

Other charge modifying techniques such as corona discharge treatments often in the presence of a reactive gas such as ammonia can also be used as is known in the art.

The interception enhancing agent comprises the cationic material in combination with a biologically active metal such that a metal colloidal complex precipitates in proximity to the positively-charged cationic material on the filter media's surface. For this purpose, the metals that are biologically active are preferred. Such biologically active metals include, but are not limited to, silver, copper, zinc, cadmium, mercury, antimony, gold, aluminum, platinum, palladium, and combinations thereof. The most preferred biologically active metals are silver and copper. The biologically active metal is exposed to the cationic material as an aqueous salt solution. The biologically active metal salt solution is preferably selected such that the metal and the counter ion of the cationic material are substantially insoluble in an aqueous environment to drive precipitation of the metal complex. Preferably, the metal is present in an amount of about 0.01% to about 2.0% by weight of the filter medium.

Particularly useful in enhancing interception of microbiological contaminants is a silver-amine-halide complex. The cationic material is preferably a homopolymer of diallyl dimethyl ammonium halide having a molecular weight of about 400,000 Daltons or other quaternary ammonium salts having a similar charge density and molecular weight. A homopolymer of diallyl dimethyl ammonium chloride useful in the present invention is commercially available from Nalco Chemical Company of Naperville, Ill., under the trade name MERQUAT® 100. The chloride counter ion may be replaced with a bromide or iodide counter ion. When contacted with a silver nitrate solution, the silver-amine-halide complex precipitates on at least a portion of the filter medium.

Once treated with the interception enhancing agent, a filter medium whose pore structure is much larger than a viral particle will provide at least 4 log reduction of viral contaminants if the fluid traverses the medium with sufficient contact time to allow the viral particles to diffuse to the surface of the filter.

The filter medium can also be treated with one or more biologically active agents known in the art. Such compounds include, but are not limited to, triclosan, a biguanide such as SURFACINE®, and BIOSHIELD®, an organosilane product including approximately 5% by weight octadecylaminodimethyltrimethoxysilylpropyl ammonium chloride and less than 3% chloropropyltrimethoxysilane.

Balancing On-Demand Performance with Sufficient Contact Time for Adequate Interception of Sub-Micron Contaminants Filter media especially preferred for a filter system of the present invention have a microporous structure wherein the mean flow path is less than about 2 microns, are treated with the interception enhancing agent, a charge modifier or a biologically active agent, and wherein the log reduction of certain contaminants is directly related to the contact time of the influent with the filter medium and not to a thickness of the filter medium. Due to the requisite contact time, the average interception of small contaminants by the filter can be prohibitively low if the flow rate of the fluid is not maintained below a required limit. Therefore, to meet on-demand or instantaneous performance levels, a filter system of the present invention should utilize a storage buffer that serves to isolate the operation of the filter from short term demands for flow that would exceed the limited flow rate required to obtain an adequate degree of contaminant interception.

The filter system includes a means for providing sufficient contact time of the influent with the filter medium. Such means include, but are not limited to, flow regulators, flow restricting orifices, flow controllers, pressure regulators, pressure controllers, or any device that can control the flow of the influent through the filter medium below or at a downstream requirement level. A storage buffer downstream of the filter is used to store the filtered effluent to meet the demand for purified fluid without regard to the average flow rate required to sustain optimal performance of the diffusion-based filter medium. This system works best in situations where the filtered effluent is needed sporadically, but the filter medium can operate at a limited average flow rate to provide adequate fluid filtration and has sufficient time to replenish the storage buffer between periods of demand. Also, by restricting the flow rate through the filter to provide the requisite contact time, in combination with the storage buffer to meet demand requirements, the size of the filter medium can be miniaturized since reduction of contaminants, including microbiological contaminants, is dependent upon contact time which is the ratio of the filter size to process flow rate.

Therefore, to provide a purified effluent substantially free of sub-micron contaminants, the influent is contacted with a filter medium operating by diffusion wherein the contaminant reduction is dependent upon the contact time of the influent with the filter medium. The flow of the influent through the filter is regulated to provide sufficient contact time between the influent and filter medium for adequate interception of the contaminants. A storage vessel collects the purified effluent to buffer the instantaneous demands of a user independent of the average flow rate of fluid through the filter medium.

To produce an exemplary diffusion-based filter medium, activated carbon is treated with a cationic material consisting of a homopolymer of dially dimethyl ammonium halide followed by precipitation of a biologically active metal against the halide counter ion associated with the cationic material. In particular, granular 12×40 mesh bituminous coal-based activated carbon having a surface area of about 950 m²/g is contacted with a solution of the cationic material in deionized water containing 3% by weight of the cationic material based on the dry weight of the carbon. This mixture is agitated for about 10 to 15 minutes and then a solution of silver nitrate containing about 0.5% by weight of the dry carbon is added. During this process, the cationic material is first adsorbed by the activated carbon. Next, the soluble silver ions precipitate with the halide counter ions associated with the cationic material to produce silver halide colloidal particles formed in proximity to the cationic material.

To demonstrate the importance of diffusion in filtration, a series of activated carbon blocks was produced from the treated coal-based activated carbon. First, the carbon granules were reduced in size to particles retained between 80 and 325 mesh screens mixed with approximately 22% by weight of particles smaller than those retained on a 325 mesh screen. These particles were mixed with about 18% by weight of a thermoplastic binder consisting of FN510 MICROTHENE® available from Equistar Corporation of Tuscola, Ill.

The mixture of activated carbon and binder are extruded in accordance with the method described in U.S. Pat. Nos. 5,019,311 and 5,189,092, to form a variety of different-size cylindrical carbon blocks. Each block is formed to produce a structure that demonstrates a mean flow path of about 0.9 to about 1.1 micrometers when measured using a porometer available from PMI, Inc., of Ithaca, N.Y. Hence, all of the blocks have nearly identical pore structure.

Figure 2:
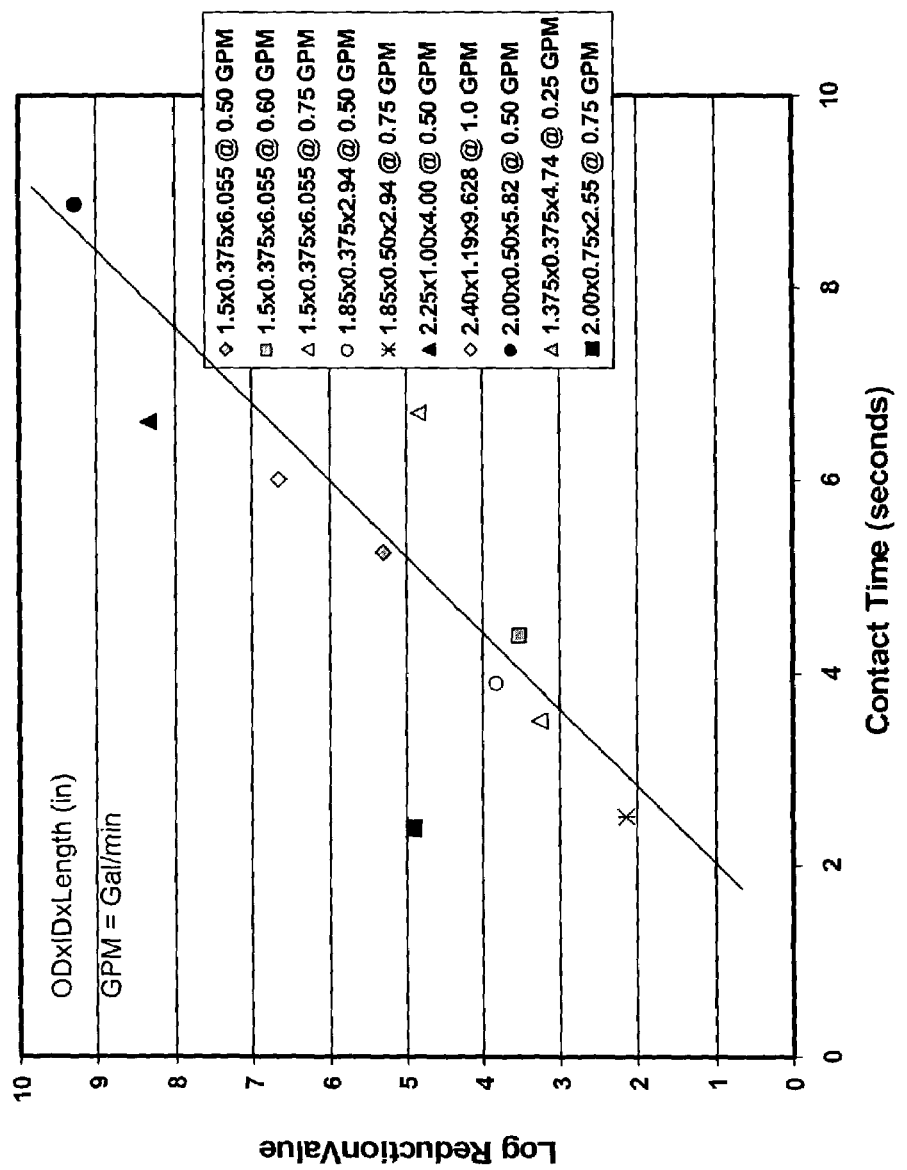

The blocks are then mounted onto end caps that allow the devices to fit within a filter housing and be tested with different particulate challenges. Tests with a wide variety of bacteria demonstrate that these carbon blocks substantially remove bacterial roughly the same size as the pore structure (data not shown). However, the interception of MS2 bacteriophage viral particles only 25 nanometers in diameter demonstrates widely varying performance for the different carbon blocks operated under different conditions. FIG. 1 shows that this MS2 viral particle reduction has no clear relationship with the thickness of the filter wall. Because all of the carbon blocks have nearly identical pore structure, this implies that an ordinary direct interception mechanism is not operating in this case. FIG. 2 shows that the MS2 viral particle interception closely responds instead to the contact time (empty bed contact time) of the fluid in contact with the filter medium. The interception improves logarithmically with contact time roughly demonstrating one-log of particle reduction for each second of empty bed contact time between the fluid carrying the particles and the filter medium.

An exemplary application of the present invention is using the filter system of the present invention within refrigerator water filtration systems. Since size is always a concern in designing appliances, a filter system that provides microbiological interception of water without the bulk of a large filter device is advantageous. Furthermore, refrigerators with a water filtration system typically have a storage vessel of some type that is used to chill the purified fluid. This reservoir can be modified to serve as a buffer that stores fluid that is slowly purified by the filter, but can provide a rapid flow of purified fluid upon demand. Thus, a user in need of filtered water would not be inconvenienced by the slow rate of filtration needed for microbiological interception. Such a reservoir can incorporate a bladder that expands and maintains the purified fluid at elevated pressure.

While the present invention has been particularly described, in conjunction with a specific preferred embodiment, it is evident that many alternatives, modifications and variations will be apparent to those skilled in the art in light of the foregoing description. It is therefore contemplated that the appended claims will embrace any such alternatives, modifications and variations as falling within the true scope and spirit of the present invention.

What is claimed is:

1. A filtration system comprising:
 a filter medium that removes particulate contaminants from a fluid by diffusion, said filter medium including membranes, nanofibers, or small particles and powder immobilized in a solid structure including an interception enhancing agent comprising a cationic material having a counter ion associated therewith, wherein a biologically active metal is precipitated with the counter ion in direct proximity to the cationic material;
 means for providing sufficient contact time for an influent to contact said filter medium such that said filtration system operates at an average flow rate sufficient to achieve a particulate reduction target performance and below a flow rate required by a downstream requirement for a purified fluid; and
 a storage buffer, downstream from said filter medium, that allows the purified fluid to be supplied at the flow rate required by the downstream requirement for a purified fluid.

2. The filtration system of claim 1 wherein said means for providing sufficient contact time comprises a flow regulator, a flow controller, a flow-restricting orifice, a pressure regulator or a pressure controller.

3. The filtration system of claim 1 wherein the filter medium includes a cationic material is selected from the group consisting of quaternized amines, quaternized amides, quaternary ammonium salts, quaternized imides, benzalkonium compounds, biguanides, cationic aminosilicon compounds, cationic cellulose derivatives, cationic starches, quaternized polyglycol amine condensates, quaternized collagen polypeptides, cationic chitin derivatives, cationic guar gum, cationic melamine-formaldehyde acid colloids, inorganic treated silica colloids, polyamide-epichlorohydrin resin, cationic acrylamides, polymers and copolymers thereof, and combinations thereof.

4. The filtration system of claim 1 wherein the cationic material is a homopolymer of diallyl dimethyl ammonium halide.

5. The filtration system of claim 1 wherein the biologically active metal is silver, copper, zinc, cadmium, mercury, antimony, gold, aluminum, platinum, palladium, or combinations thereof.

6. The filtration system of claim 1 wherein said filter system is located in a refrigerator.

7. A filtration system comprising:
 a filter medium including an interception enhancing agent comprising a cationic material having a counter ion associated therewith, wherein a biologically active metal is precipitated with the counter ion in direct proximity to the cationic material;
 a flow regulator for providing sufficient contact time of an influent with said filter medium; and
 a storage buffer for storing a purified effluent to provide on-demand access to the purified effluent independent of the flow rate through said filter medium needed to achieve a required contact time.

8. The filtration system of claim 7 wherein said filter medium provides at least 4 log reduction in microbiological contaminants.

9. The filtration system of claim 7 wherein said system is located within a refrigerator.

10. A method of providing a purified fluid on-demand comprising the steps of:

providing a filtration system including a filter medium that removes particulate contaminants by diffusion, said filter medium including membranes, nanofibers, or small particles and powder immobilized in a solid structure including an interception enhancing agent comprising a cationic material having a counter ion associated therewith, wherein a biologically active metal is precipitated with the counter ion in direct proximity to the cationic material;

operating the filtration system at an average flow rate below that of a rate demanded by a user such that a sufficient contact time is provided for adequate diffusive filtration; and collecting a purified fluid in a storage vessel to buffer an intermittent instantaneous demand independent from the average flow rate through the filter medium.

11. The method of claim 10 wherein in the step of operating the filtration system at the average flow rate, a flow orifice is used to maintain a contact time sufficient to allow particulate contaminants in the fluid to diffuse to a surface of the filter medium.

* * * * *